(12) United States Patent
Gault

(10) Patent No.: US 10,130,402 B2
(45) Date of Patent: Nov. 20, 2018

(54) BONE FIXATION DEVICES HAVING A LOCKING FEATURE

(71) Applicant: GLOBUS MEDICAL, INC., Audubon, PA (US)

(72) Inventor: James A. Gault, Philadelphia, PA (US)

(73) Assignee: Globus Medical, Inc., Audubon, PA (US)

( * ) Notice: Subject to any disclaimer, the term of this patent is extended or adjusted under 35 U.S.C. 154(b) by 357 days.

(21) Appl. No.: 14/864,999

(22) Filed: Sep. 25, 2015

(65) Prior Publication Data

US 2017/0086892 A1 Mar. 30, 2017

(51) Int. Cl.
*A61B 17/80* (2006.01)

(52) U.S. Cl.
CPC ...... *A61B 17/8038* (2013.01); *A61B 17/8033* (2013.01); *A61B 17/8047* (2013.01)

(58) Field of Classification Search
CPC ............ A61B 17/7044; A61B 17/7091; A61B 17/8028; A61B 17/8047; A61B 17/8052
See application file for complete search history.

(56) References Cited

U.S. PATENT DOCUMENTS

| | | | | |
|---|---|---|---|---|
| 5,810,823 | A | * 9/1998 | Klaue | A61B 17/8028 606/289 |
| 8,486,116 | B2 | * 7/2013 | Heilman | A61B 17/8047 606/286 |
| 2006/0036249 | A1 | 2/2006 | Baynham et al. | |
| 2006/0149253 | A1 | 7/2006 | Doubler et al. | |
| 2009/0105831 | A1 | 4/2009 | Jones et al. | |
| 2013/0165981 | A1 | * 6/2013 | Clasbrummel | A61B 17/8033 606/289 |

FOREIGN PATENT DOCUMENTS

KR 1020110021142 A 3/2011

* cited by examiner

*Primary Examiner* — Anu Ramana

(57) ABSTRACT

Devices and methods for locking one or more bone screws to a fixation plate. A cam-style locking feature may be disposed in the fixation plate such that, when the locking feature is in a first position, the bone screw is able to traverse an opening in the fixation plate and engage adjacent bone; and when the locking feature is rotated into a second position, an interference between the locking feature and bone screw causes the bone screw to be firmly secured to the fixation plate.

16 Claims, 7 Drawing Sheets

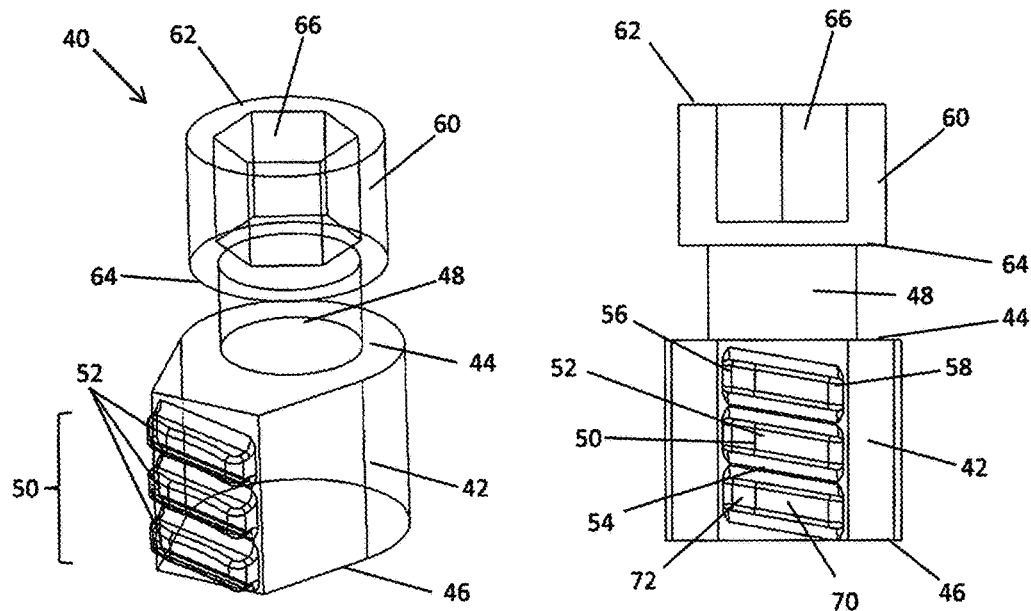
FIG. 4A
FIG. 4B
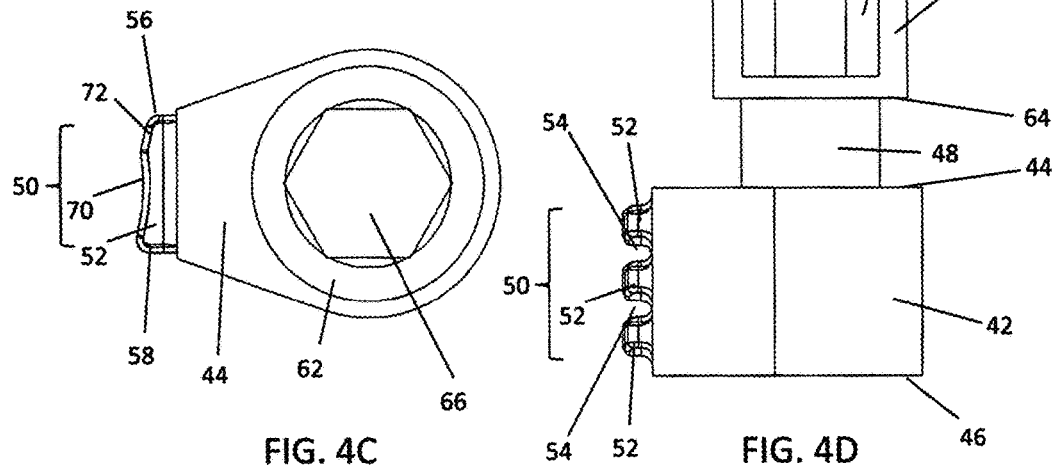
FIG. 4C
FIG. 4D

BONE FIXATION DEVICES HAVING A LOCKING FEATURE

FIELD OF THE INVENTION

The present disclosure generally relates to devices and methods for securing one or more fasteners in a fixation plate. For example, a rotational locking mechanism may be provided to lock a bone screw positioned within a fixation plate.

BACKGROUND OF THE INVENTION

Spinal fixation has become a common approach in treating spinal disorders, fractures, and for fusion of vertebrae, for example, in cases of trauma, tumors, and degenerative conditions. A common device used for spinal fixation is a bone fixation plate. A typical bone fixation plate includes a relatively flat, rectangular plate having a plurality of apertures therethrough. A corresponding plurality of fasteners, such as bone screws, are provided to secure the bone fixation plate to one or more bones, such as two adjacent spinal vertebrae.

A common problem associated with the use of such fixation plates, however, is the tendency of the bone screws to "back out" of the underlying bone under the stress of bodily movement. This problem occurs primarily due to the normal motion of the body, but may be particularly prevalent in areas of high stress, such as, for example, in the spine. Given the delicate nature of the spine, any post-operative fixation plate movement may not only frustrate the surgical goals, but may also raise patient safety concerns.

A number of various designs have been brought forth in attempts to lock the screws to the bone fixation plate, prevent screws from pulling away from the bone, or to prevent the screws from backing out or pulling away from the bone fixation plate. While there are many designs in this area, it is desirable to have improved locking devices and systems having locking features integrated with the bone plate, which have enhanced functionality and ease of use.

SUMMARY OF THE INVENTION

To meet this and other needs, devices, systems, and methods for locking one or more fasteners in a device, such as a fixation plate, are provided. In particular, a rotational locking mechanism is provided with a cam-style locking feature to provide secure locking of the fastener into the fixation plate. As the locking mechanism is rotated, engagement of the cam-style locking feature with a portion of the fastener (e.g., a plurality of threads) increases because the radius of the locking feature on the locking mechanism increases. The locking mechanism may also be constrained within the fixation plate to provide for enhanced attachment. The configuration of the fixation plate and locking mechanism allow for secure locking of the fastener to the plate.

According to one embodiment, an assembly for locking a fastener in a fixation plate is provided. The fastener has a plurality of threads. For example, the fastener may be in the form of a bone screw having a head and a shaft extending therefrom, the shaft may have the plurality of threads thereon. The assembly includes a locking element at least partially positioned in the fixation plate. The locking element has a base member and a head portion. The base member has an interlock portion configured to engage the threads of the fastener when in a locked position. The head portion extends from the base member, and the head portion is configured to be engaged by a driver to rotate the base member from an unlocked position to the locked position.

The interlock portion may include a cam-style locking feature. For example, the interlock portion may include a plurality of elongated protrusions having a recess positioned between adjacent protrusions. In one embodiment, the interlock portion includes three substantially parallel protrusions. The elongated protrusions may be angled such that they correspond substantially to the thread angle of the threads of the fastener (e.g., about 60 degrees). When in the unlocked position, there is no interference between the elongated protrusions and the fastener. When in the locked position, there is interference between the elongated protrusions and the shaft of the fastener. In particular, an outer surface of each of the plurality of elongated protrusions contacts the shaft of the fastener and the recesses positioned between adjacent protrusions receive a portion of the plurality of threads of the fastener.

The locking mechanism may also be constrained within the fixation plate. For example, base member and/or head portion of the locking mechanism may be positioned inside the fixation plate, for example, in a blind opening in the fixation plate. In one embodiment, the locking element includes a shaft between the base member and the head portion. The shaft may have a smaller diameter than the head portion of the locking element. The head portion and shaft may fit within a corresponding notch, recess, and/or ridge positioned inside the blind opening in the fixation plate. Alternatively, the locking mechanism may be threaded into the fixation plate.

According to another embodiment, a system for preventing a bone screw from backing out of a fixation plate includes a fastener, a locking element, and a fixation plate. The fastener has a plurality of threads. The locking element includes a base member and a head portion. The base member has an interlock portion configured to engage the threads of the fastener when in a locked position, and the head portion extends from the base member. The head portion is configured to be engaged by a driver to rotate the base member from an unlocked position to the locked position. The fixation plate has a bottom surface configured to engage a portion of the bone being fixated, an opposite top surface, an opening defined therethrough sized and configured to receive at least a portion of the fastener, and a blind opening for receiving the locking element positioned adjacent to the opening for receiving the fastener. The blind opening may include a ridge configured to prevent the locking element from being removed axially. The ridge may be configured to engage a bottom surface of the head portion, for example.

According to another embodiment, a method of locking a bone screw in a fixation plate may include: inserting a fastener through an opening in a fixation plate and into contact with bone, the fastener having a plurality of threads configured to engage the bone; and locking the fastener to the fixation plate by rotating a locking element in the fixation plate to a locked position such that an interlock portion on the locking element engages at least a portion of the plurality of threads of the fastener. For example, a driver may engage a recess in the locking element to rotate the locking element. The method may also include, before the fastener is inserted in the fixation plate, placing the locking element through the opening in the fixation plate and sliding the locking element over such that the locking element is seated in the blind opening in the fixation plate.

According to yet another embodiment, a method of manufacturing a fixation plate with an integrated locking element may include: providing a locking element having a base member with an interlock portion configured to engage the threads of a fastener when in a locked position, a head portion configured to be engaged by a driver to rotate the base member from an unlocked position to the locked position, and a shaft connecting the base member to the head portion; and inserting the locking element axially through a fastener opening in the fixation plate and sliding the locking element transversely into a blind opening in the fixation plate such that the locking element is seated in the blind opening in the fixation plate.

BRIEF DESCRIPTION OF THE DRAWING

A more complete understanding of the present invention, and the attendant advantages and features thereof, will be more readily understood by reference to the following detailed description when considered in conjunction with the accompanying drawings wherein:

FIGS. 4A-4D provide alternative views of the locking element;

DETAILED DESCRIPTION

Figure 1:
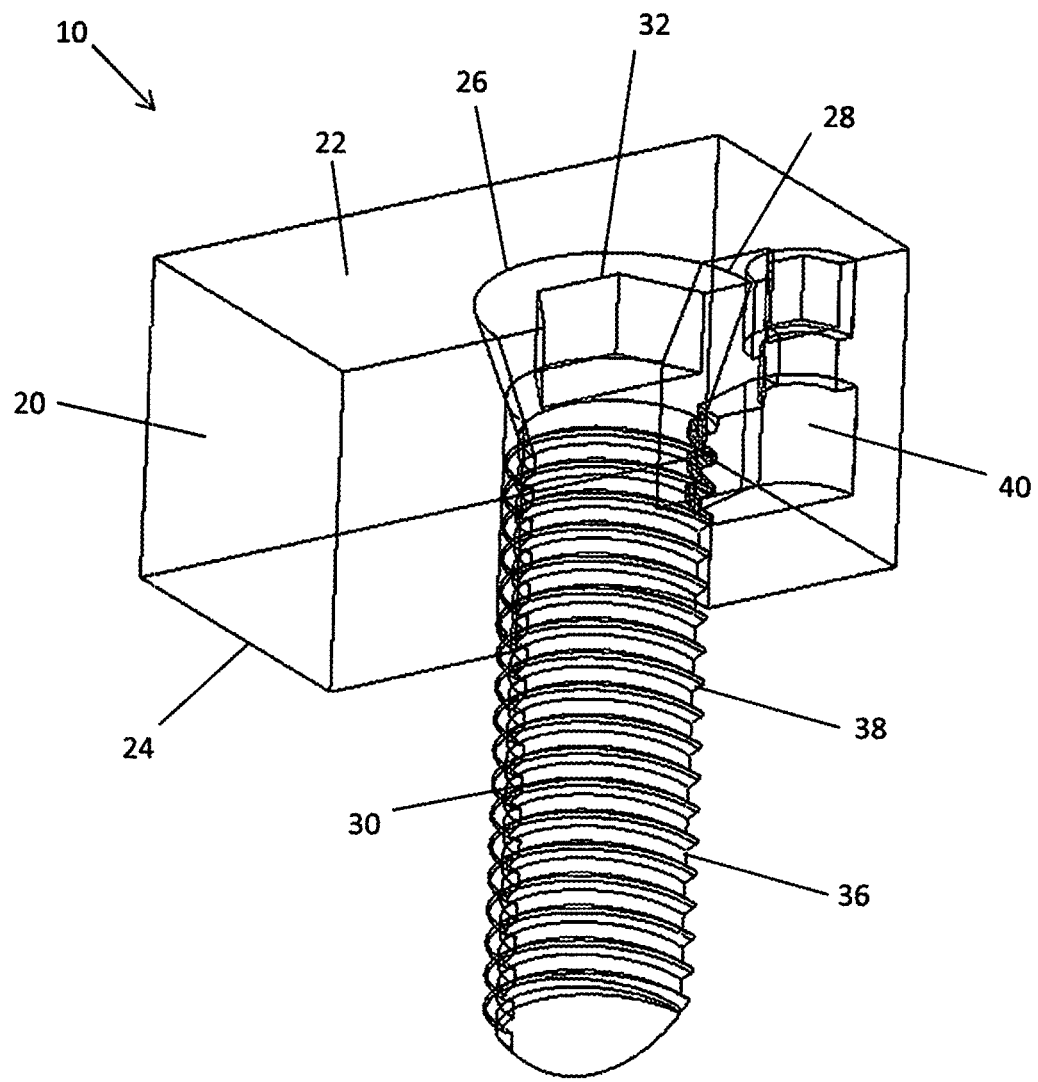
FIG. 1 depicts a perspective cross-sectional view of a fixation plate, fastener, and locking construct according to one embodiment.

Embodiments of the disclosure are generally directed to devices, systems, and methods for locking one of more fasteners, such as bone screws, in a fixation plate. Specifically, a cam-style locking feature may be disposed in the plate such that, when the locking feature is in a first position, the bone screw is able to traverse an opening in the fixation plate and engage adjacent bone; and when the locking feature is rotated into a second position, an interference between the locking feature and bone screw causes the bone screw to be secured firmly to the fixation plate.

Although described with reference to fixation plates, it will be appreciated that any suitable fixation device, such as interbody devices, frames, cages, spacers, standalone implants, and the like may also incorporate the locking features described herein. Similarly, although bone screws are exemplified in this document, it will also be appreciated that other suitable fasteners, such as shims, nails, and the like, may be adapted to mate with the locking features described herein. These devices may be suitable for fixation into areas along the spine, such as one or more vertebrae; a hip bone, such as an ilium; a leg bone, such as a femur; or a bone from an arm, such as a distal forearm bone or a proximal humerus; or any other bone in a mammal. When used in the spine, the fixation devices may be suitable for cervical, thoracic, lumbar, or sacral regions and may be surgically approached anteriorly, posteriorly, laterally, anterolaterally, or the like.

The embodiments of the disclosure and the various features and advantageous details thereof are explained more fully with reference to the non-limiting embodiments and examples that are described and/or illustrated in the accompanying drawings and detailed in the following description. The features of one embodiment may be employed with other embodiments as the skilled artisan would recognize, even if not explicitly stated herein. Descriptions of well-known components and processing techniques may be omitted so as to not unnecessarily obscure the embodiments of the disclosure. The examples used herein are intended merely to facilitate an understanding of ways in which the disclosure may be practiced and to further enable those of skill in the art to practice the embodiments of the disclosure. Accordingly, the examples and embodiments herein should not be construed as limiting the scope of the disclosure, which is defined solely by the appended claims and applicable law. Moreover, it is noted that like reference numerals represent similar features and structures throughout the several views of the drawings.

Figure 2:
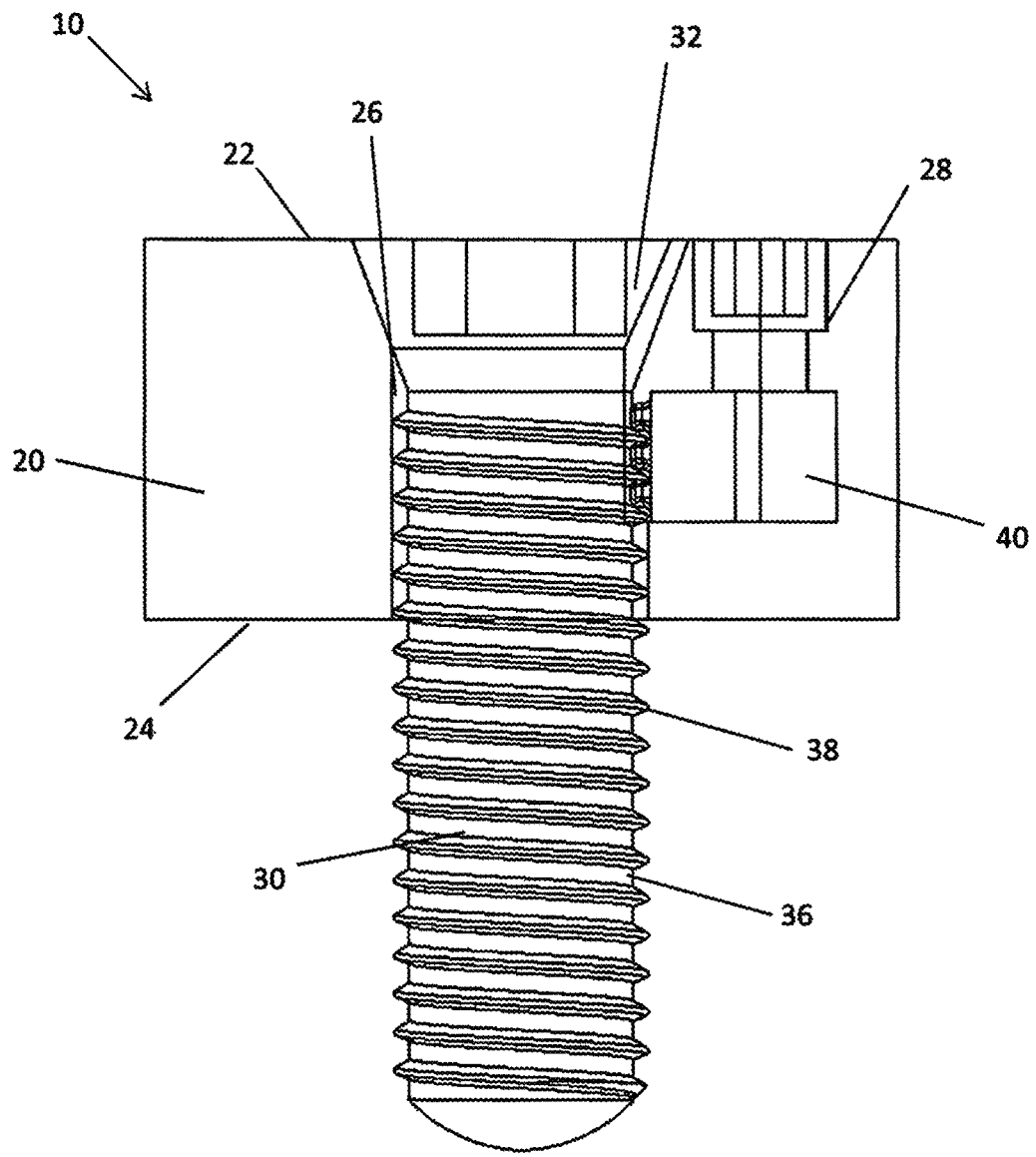
FIG. 2 depicts a partial cross-sectional view of the embodiment shown in FIG. 1.

Referring now to the drawing, FIGS. 1 and 2 depict a system 10 for locking a fastener 30 in a fixation plate 20, for example, in order to lock the fastener 30 to the bone fixation plate 20, prevent the fastener 30 from pulling away from the bone, and/or to prevent the fastener 30 from backing out or pulling away from the bone fixation plate 20. The system 10 includes fixation plate 20, one or more fasteners 30, and one or more locking elements 40. Although system 10 is exemplified with a single fastener 30 and single locking element 40, it will be understood that additional fasteners 30 and/or locking elements 40, which may be the same or different, may be used with plate 20. For example, two or more, three or more, four or more, or any suitable number of fasteners 30 and/or locking elements 40 may be selected to secure the plate 20 to the bone based on the surgical necessity.

As best seen in FIG. 1, the fixation plate 20 has a top surface 22 and a bottom surface 24 configured to contact and/or engage a portion of the bone being fixated (not shown). Although identified as top and bottom surfaces 22, 24, respectively, it will be appreciated that the fixation plate 20 may be oriented in any suitable way for appropriate bone fixation and stabilization. The fixation plate 20 includes one or more apertures or openings 26 defined therethrough. For example, the opening 26 may extend from the top surface 22 to the bottom surface 24 of the plate 20. The opening 26 is sized and configured to receive at least a portion of the fastener 30. In particular, the opening 26 may include a wider portion to receive the head 32 of the fastener 30 and a narrower portion to receive a portion of the shaft 36 of the fastener 30. Accordingly, the top of the head 32 may be flush with or recessed below the top surface 22 of the fixation plate 20. Because the locking element 40 can engage with the fastener 20 at any position along the length of the fastener 20, the head 32 of the fastener 20 does not need to be flush with the plate 20.

The plate 20 may also include a blind hole or opening 28 for receiving the locking element 40. The blind opening 28 is positioned adjacent to the opening 26 for receiving the fastener 30. The blind opening 28 may extend from the top surface 22 to a distance in the fixation plate 20, but preferably does not extend completely through to the bottom surface 24 of the plate 20. The blind opening 28 is shaped and dimensioned to receive the locking element 40. The locking element 40 may be positioned in the blind opening 28 such that a top surface 62 of the locking element 40 may be flush with or recessed below the top surface 22 of the fixation plate 20. The blind opening 28 may be continuous with the fastener opening 26, for example, forming a single contiguous opening in the fixation plate 20. Although not shown, the plate 20 may include multiple fastener openings 26 with adjacent blind openings 28 for receiving locking elements 40 to lock each respective fastener 30 in the plate 20. Each fastener 30 may be provided with a separate locking element 40.

Any fastener 30 known in the art may be used. For example, the fastener 30 may include bone screws, shims, nails, or other fastening devices having at least one threaded portion 38. The fasteners 30 may be poly-axial screws, uniplanar screws, mono-axial screws, or the like based on their desired adjustability and functionality. The preferred fastener 30 has a plurality of threads 38. For example, the fastener 30 may be in the form of a bone screw having shaft 36 extending from the head 32. The plurality of threads 38 may extend from the base of head 32 to a distal tip of the shaft 36. Alternatively, the plurality of threads 38 may extend along a portion of the shaft 36. The head 32 may be conical, rounded, spherical, or the like. The head 32 may be enlarged relative to the shaft 36. Preferably, the head 32 is sized and dimensioned such that it lies flush with or is recessed in the top surface 22 of the plate 20. The head 32 may also include a recess 34 configured to receive a driving instrument (e.g., a hex driver), for example, to apply rotational force to the fastener 30 such that at least a portion of the shaft 36 can be secured into bone.

Figure 3:
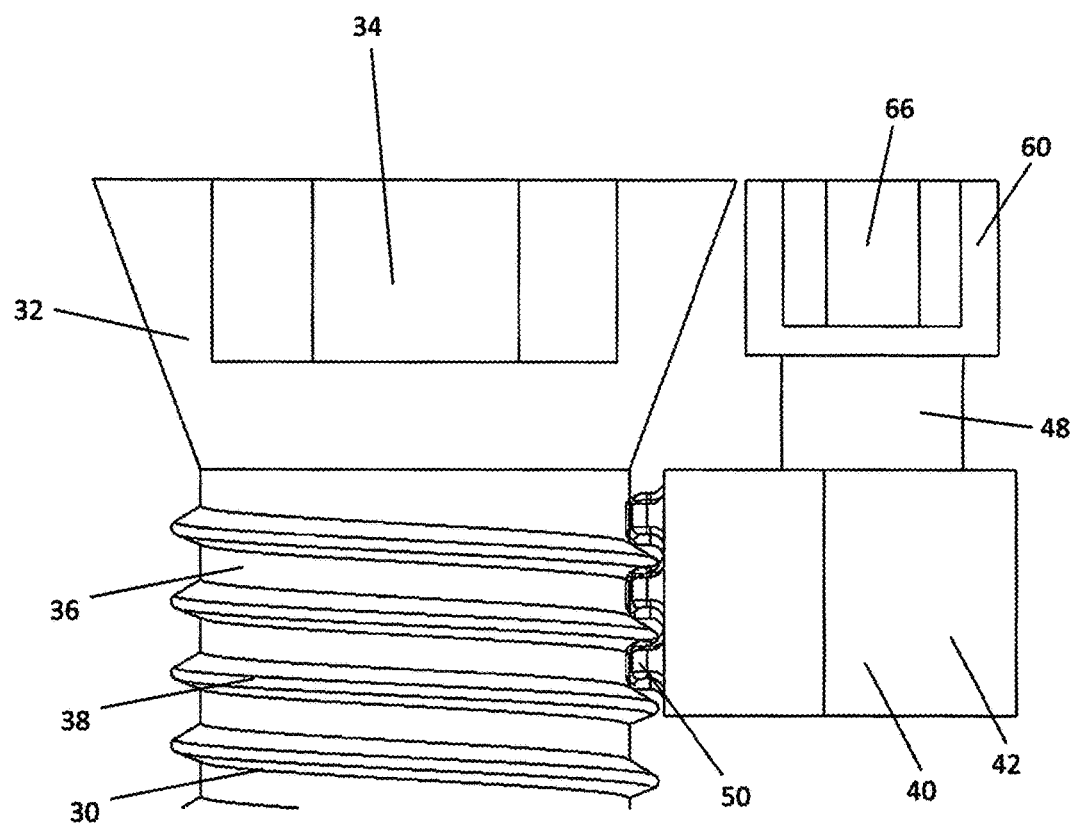
FIG. 3 depicts a close up view of the interaction between the fastener and the locking element.

As shown in FIG. 3, the locking element 40 is configured to secure and lock the fastener 30 to the plate 20 when in a locked position. The locking element 40 includes a head portion 60 configured to rotate the locking element 40 and a base member 42 having an interlock portion 50 configured to engage the fastener 30, when rotated into the locked position. The interlock portion 50 is configured to engage the threads 38 and/or shaft 36 of the fastener 30. For example, the interlock portion 50 may be configured to engage an upper portion of the shaft 36 and an upper portion of the threaded section 38 of the fastener 30. In this embodiment, the interlock portion 50 does not engage the head 32 of the fastener 30 and rests below the head 32 of the fastener 30. It is envisioned, however, that the interlock portion 50 could intermesh with threads on the head 32 of the fastener 30, if threads were present (not shown).

One advantage of system 10 is that the interlock portion 50 of the locking element 40 can engage with the fastener 30 at any position along the length of the fastener 30. As the locking element 40 is rotated, a force is generated on the fastener 30 that is perpendicular to a longitudinal axis of the fastener 30, which may come from the interference between the interlock portion 50 and the shaft 36 of the fastener 30. The interlock portion 50 also interacts with the threads 38 of the fastener 30 to further tighten the fastener 30 to the plate 20.

As best illustrated in FIGS. 4A-4D, the locking element 40 has a head portion 60 extending from base member 42. The head portion 60 extends from a top surface 62 to a bottom surface 64. The head portion 60 may be substantially cylindrical in shape or of any other suitable shape. The head portion 60 of the locking element 40 may be positioned in the blind opening 28 of the plate 20 such that the top surface 62 of the locking element 40 is at least flush with or recessed below the top surface 22 of the fixation plate 20. In other words, the locking element 40 may be positioned completely inside the plate 20. The head portion 60 may include a recess 66, for example, positioned in top surface 62, which is configured to be engaged by a driving instrument (e.g., a hex driver), to rotate the base member 42 between unlocked and locked positions.

The base member 42 of the locking element 40 extends from a top surface 44 to a bottom surface 46. One or more sidewalls may connect the top surface 44 to the bottom surface 46. The sidewalls may be curved, rounded, straight, or the like such that the base member 42 has a partially cylindrical shape or any other suitable shape. For example, the base member 42 may have a generally tear drop shape when viewed from a top-down view (FIG. 4C). The base member 42 may have a larger footprint than the head portion 60 of the locking element 40. The interlock portion 50 may be positioned along one of the sidewalls extending from the top surface 44 to the bottom surface 46 of the base member 42. In one embodiment, the locking element 40 includes a shaft 48 between the base member 42 and the head portion 60. The shaft 48 may also be generally cylindrical in shape. The shaft 48 may have a smaller relative diameter than the head portion 60 and/or base member 42 of the locking element 40. The shaft 48 may be a separate component or may be in the form of an annular recess or groove cut into a bottom portion of the head portion 60 and/or an annular recess or groove cut into a top portion of the base member 42.

The base member 42 includes interlock portion 50 configured to engage the threads 38 and/or shaft 36 of the fastener 30 when in the locked position. The interlock portion 50 may include a cam-style locking feature. For example, the cam-style interlock portion 50 may have at least two relative positions. In a first orientation, where the locking element 40 is unlocked, the interlock portion 50 does not intermesh with the threads 38 of the fastener 30 although a portion of the threads 38 may be permitted to travel through at least a portion the interlock portion 50. In the first orientation, the fastener 30 is free to travel through the opening 26 in the plate 20. In a second orientation, where the locking element 40 is locked, the interlock portion 50 is intermeshed with the threads 38 and/or shaft 36 of the fastener 30 to cause interference between them. This prevents or minimizes any further rotation of the fastener 30, thereby preventing or inhibiting back out of the fastener 30 from the plate 20.

As seen in FIGS. 4A-4D, the interlock portion 50 may include a plurality of elongated protrusions 52 having an elongate recess 54 positioned between respective adjacent protrusions 52. The protrusions 52 may be sized and dimensioned to fit between the threads 38 of the fastener 30 and the recesses 54 may be sized and dimensioned to receive the threads 38 of the fastener 30. The interlock portion 50 may include two or more, three or more, or four or more protrusions 52 each having a corresponding recess 54 positioned therebetween. In the embodiment shown, the interlock portion 50 includes three substantially parallel protrusions 52. The interlock portion 50 may contain more or less protrusions 52 depending on the type of fastener 30 including the pitch, lead, thread angle, and the like being used.

As evident in FIG. 4C, each protrusion 52 extends from a first end 56 to a second end 58 along a front face of the base member 42. The protrusion 52 is preferably not uniform in depth or thickness between the first and second ends 56, 58 in order to provide the cam-style functionality of the interlock portion 50. In other words, an outer most surface 70 for each protrusion 52 has a cam-like profile. The outer surface 70 may have a slightly curved or contoured surface extending from the first end 56 to the second end 58. For example, the first end 56 may have a smaller depth or thickness relative to the second end 58. In particular, the diameter of the contoured surface may be sized to match the diameter of the shaft 36 of the fastener 30 to allow the locking element 40 to snap into place. In addition, proximate to the first end 56 of each protrusion 52, a notch or bevel 72 may be provided in the outer surface 70 of the protrusion 52 such that the fastener 30 is able to rotate freely without engaging the locking element 40. In this configuration, the recesses 54 of the interlock portion 50, positioned between adjacent protrusions 52, may be able to receive a portion of the plurality of threads 38 of the fastener 30, but there is no interference of the fastener 30 with the interlock portion 50.

The cam-style outer surfaces 70 of each protrusion 52, for example, extending from beveled portion 72 to the second end 58 allow for translational and/or rotational movement of the locking element 40 into the locked position. Accordingly, when the locking element is translated, pivoted, or rotated into the locked position, at least a portion of the outer cam surface 70 (e.g., including second end 58 having a greater depth or thickness) of each of the plurality of elongated protrusions 52 contacts the shaft 36 of the fastener 38 and the recesses 54 fully receive the corresponding threads 38 of the fastener 30. This engagement may be best seen in FIG. 3. Engagement of the interlock portion 50 increases as the locking element 40 is turned because the radius increases until the recess 54 is reached, at which time the locking element 40 can snap into place. As the locking element 40 is rotated (e.g., clockwise), its engagement with the threads 38 and/or shaft 36 of the fastener 30 increases because the radius of the interlock portion 50 on the locking element 40 increase, which is similar to the functionality of a cam mechanism.

As best seen in FIG. 4B, the elongated protrusions 52 may be angled such that they correspond substantially to the pitch and/or thread angle of the threads 38 of the fastener 30. For example, the elongated protrusions 52 may be angled about 50-70 degrees, about 55 to 65 degrees, or about 60 degrees relative to an axis transverse to the longitudinal axis of the locking element 40. As shown, the protrusions 52 may be angled such that the first end 56 is higher relative to the second end 58. Although, it is contemplated that any angle or orientation may be provided to mate with the corresponding fastener 30 that is used in the plate 20. Each elongated protrusion 52 may also have a relative height and spacing of the recesses 54 may be selected between the protrusions 52 such that the protrusions 52 and recesses 54 mate and intermesh with the threads 38 of the fastener 30. As evident in FIG. 4D, the recesses 54 may be substantially curved, rounded, or beveled between each protrusion 52. The protrusions 52 may also be provided with curved, rounded, or beveled transitions at the outer most surface 70.

Figure 5A:
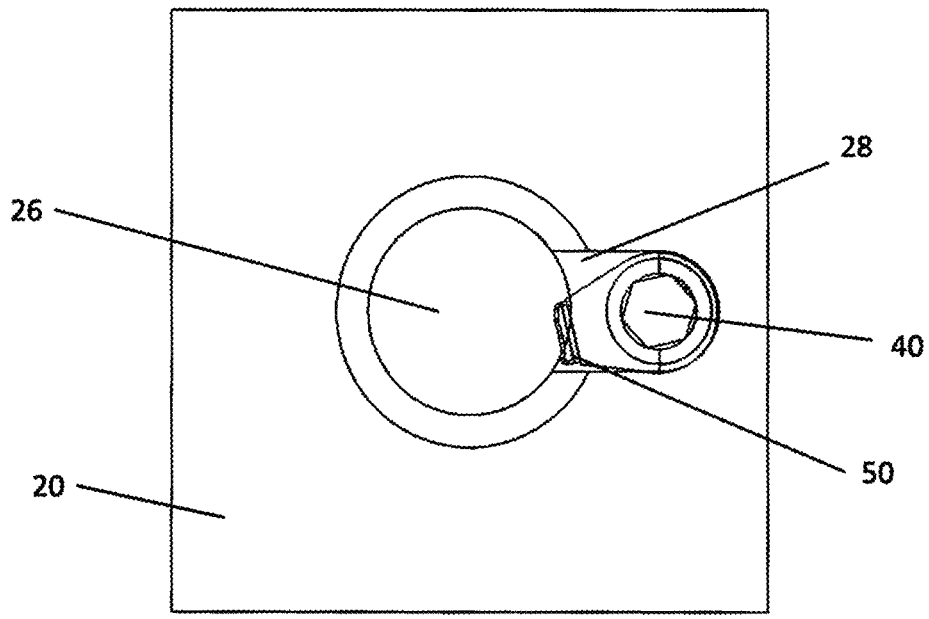
FIGS. 5A and 5B show unlocked and locked positions, respectively, of the locking element in the fixation plate.

The interlock portion 50 can be translated, pivoted, or rotated between the locked and unlocked positions. FIG. 5A depicts the unlocked position for the locking element 40. As shown, the interlock portion 50 is offset relative to the fastener opening 26 although a portion of the interlock portion 50 (e.g., beveled portion 72) is still positioned in a portion of the opening 26. When in the unlocked position, there is no interference between the interlock portion 50 and the fastener 30. In particular, when unlocked, the elongated protrusions 52 do not interfere with the fastener 30, and the fastener 30 is free to traverse the opening 26 in the plate 20 and engage bone. After the fastener 30 is secured in the bone, the locking element 40 may be rotated into the locked position. The amount of movement or rotation of the locking element 40, from unlocked to locked positions, is preferably less than 90 degrees, less than 75 degrees, or less than 60 degrees. For example, the amount of movement or rotation, between unlocked and locked positions, may range from about 5 to 60 degrees, about 10 to 45 degrees, about 20 to 40 degrees, or about 25 to 35 degrees.

Figure 5B:
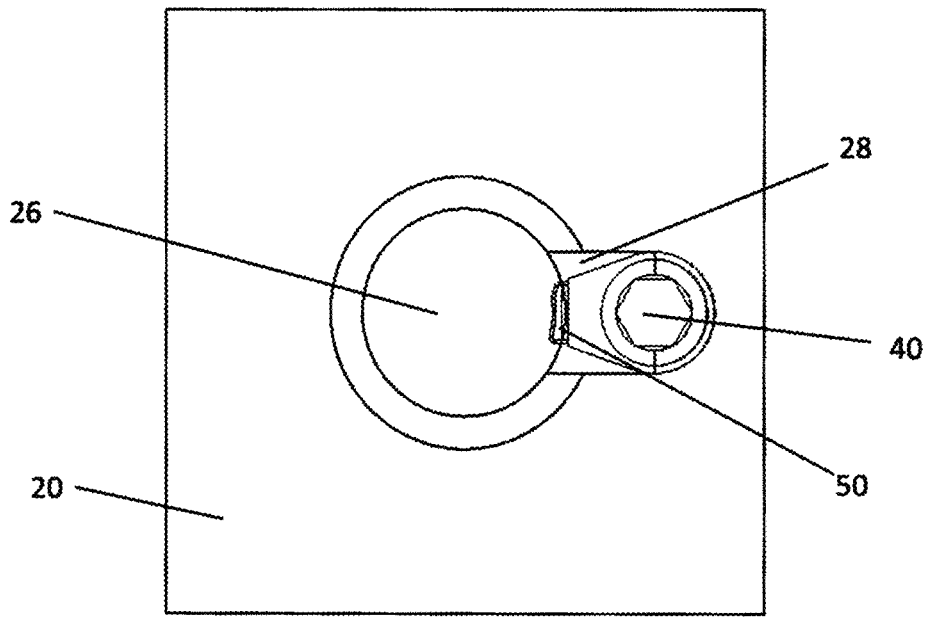

FIG. 5B depicts the locked position for the locking element 40. As shown, the interlock portion 50 is now aligned with the fastener opening 26 such that the entire interlock portion 50 is positioned inside the opening 26. When in the locked position, there is interference between the interlock portion 50 and the fastener 30, thereby preventing or minimizing rotation of the fastener 30. In particular, the elongated protrusions 52 interfere with the shaft 36 and/or the threads 38 of the fastener 30, and the fastener 30 is fixed in position. The radius of curvature of the outer surface 70 of each elongated protrusion 52 may be configured to match the radius of the shaft 38 of the fastener 30 to allow the locking element 40 to seat into the shaft 38 of the fastener 30. The interference with the shaft 36 imparts a force that is perpendicular to the longitudinal axis of the fastener 30, which acts to lock the fastener 30 into place and prevent the fastener 30 from pulling out.

Figure 6A:
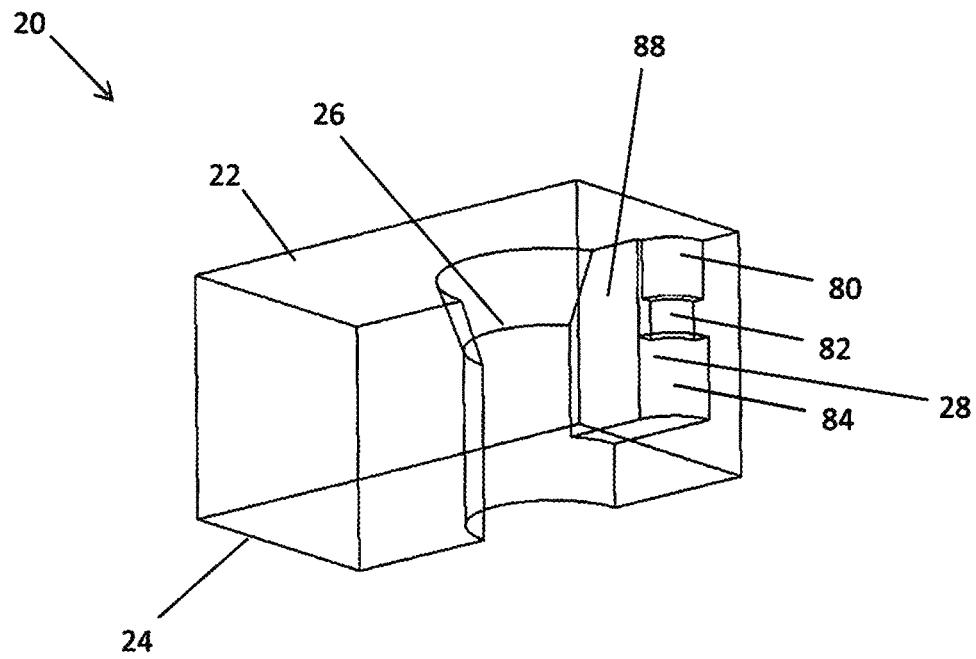
FIGS. 6A and 6B show alternative views of the fixation plate without the locking construct or fastener present.
Figure 6B:
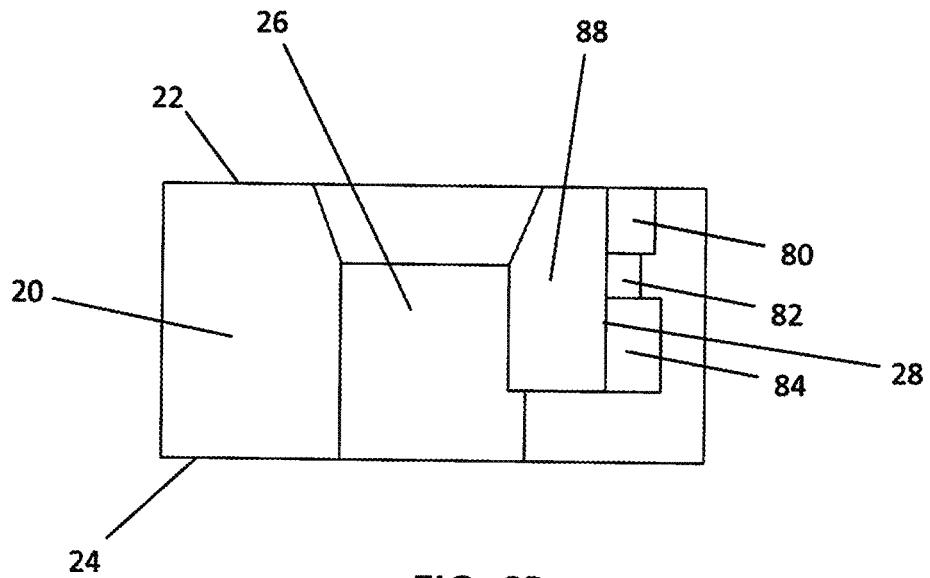

The locking element 40 may be constrained within or locked to the fixation plate 20. The locking element 40 may be at least partially positioned in the fixation plate 20. In an exemplary embodiment, the entire locking element 40 is positioned within the fixation plate 20. For example, base member 42 and/or head portion 60 of the locking element 40 may be positioned inside the fixation plate 20, for example, in the blind opening 28 in the fixation plate 20. As shown in FIGS. 6A and 6B, the blind opening 28 may include a first portion 80, second portion 82, and third portion 84. The first, second, and third portions 80, 82, 84, respectively, may be sized and dimensioned to receive the corresponding dimensions of the locking element 40. In particular, the first portion 80 may be configured to receive the head portion 60 of the locking element 40. The second portion 82 may be configured to receive the shaft 48 of the locking element 40. The second portion 82 may have a smaller diameter than the first portion 80. The second portion 82 may include or be in the form of a ridge configured to prevent the locking element 40 from being removed axially. For example, the ridge may be configured to engage the bottom surface 64 of the head portion 60 and/or top surface 44 of the base member 42 of the locking element 40. The third portion 84 may be configured to receive the base member 42 of the locking element 40. In addition, a transition portion 88 between the fastener opening 26 and the blind opening 28 may be provided to improve access between the two openings 26, 28. In an alternative embodiment (not shown), the locking element 40 may be threaded into the fixation plate 20, which would have a corresponding thread.

According to one method of locking the fastener 30 in the fixation plate 20, the fastener 30 is inserted through the opening 26 in the fixation plate 20 and into contact with bone. The fastener 30 is locked to the plate 20 by rotating the locking element 40 in the fixation plate 20 to the locked position such that the interlock portion 50 on the locking element 40 engages at least a portion of the plurality of threads 38 of the fastener 30. The locking element 40 may be engaged into locked mode, for example, by clockwise turning of the head portion 60 of the locking element. For example, a driver may engage the recess 66 in the head portion 60 of the locking element 40 to rotate the locking element 40 into position.

Figure 7A:
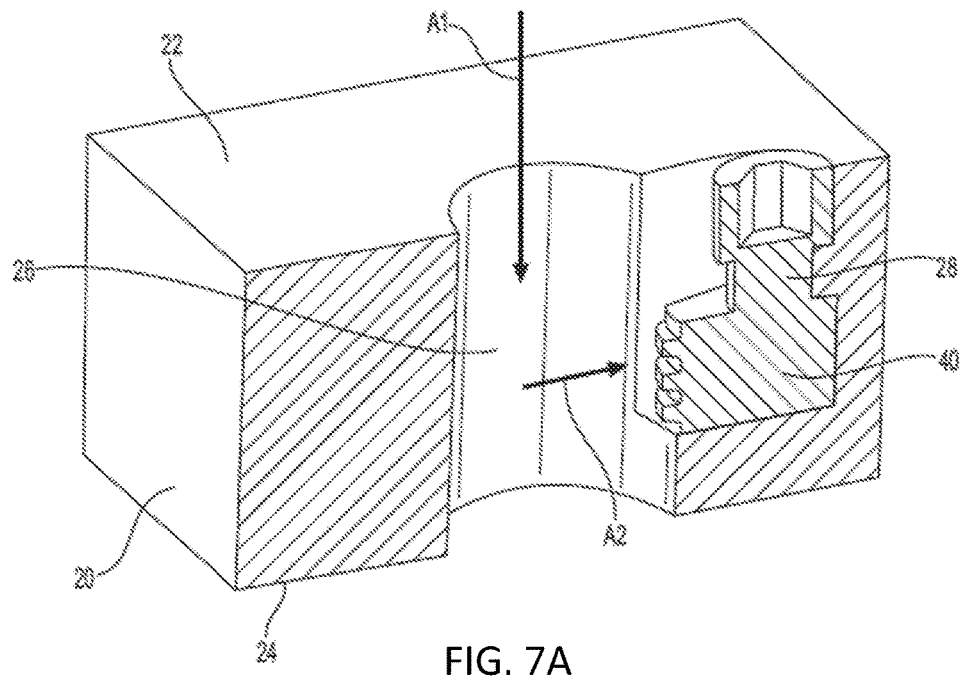
FIGS. 7A-7C show alternative views of positioning the locking element in the fixation plate.
Figure 7B:
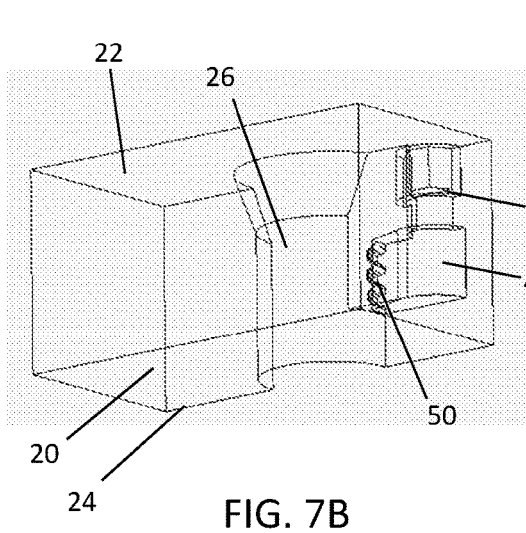
Figure 7C:
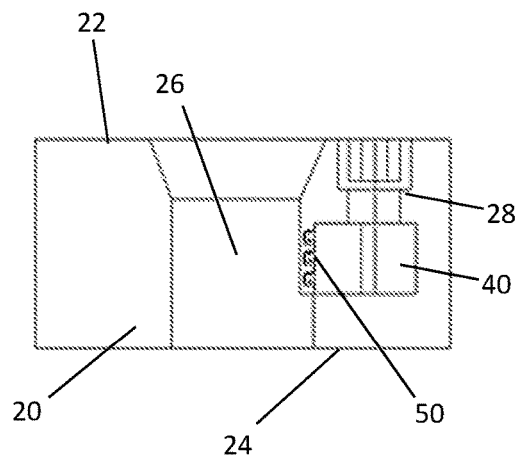

As depicted, for example, in FIGS. 7A-7C, the method may also include, before the fastener 30 is inserted in the fixation plate 20, placing the locking element 40 through the opening 26 in the fixation plate 20 and sliding the locking element 40 over such that the locking element 40 is seated in the blind opening 28 in the fixation plate 20. In particular, as shown in FIG. 7A, arrow A1 depicts the movement of the locking element 40 axially through the fastener opening 26 in the fixation plate 20 and arrow A2 depicts movement of the locking element 40 transversely into the blind opening 28 in the fixation plate 20 such that the locking element 40 is fully seated in the blind opening 28 in the fixation plate 20. In the alternative, the locking element 40 can be assembled in the plate 20 during the manufacturing process to produce a fixation plate 20 with an integrated locking element 40. Thus, during manufacturing, the locking element 40 may be inserted axially through the fastener opening 26 and slid transversely into the blind opening 28 such that the locking element 40 is seated in the blind opening 28 in the fixation plate 20. The locking element 40 may also be positioned or rotated into the unlocked position before use.

This cam-style locking element 40 provides for secure locking of the fastener 30 into the fixation plate 20. As the locking element 40 is rotated, engagement of the cam-style locking feature 50 with the threads 38 on the fastener 20 increases because the radius of the locking feature on the locking mechanism increases. The locking element 40 may also be constrained within the fixation plate 20 to provide for enhanced attachment. The configuration of the fixation plate 20, fastener 30, and locking element 40 allow for secure locking of the fastener 30 to the plate 20, thereby preventing or minimizing undesirable movement of the fastener 30.

Although the invention has been described in detail and with reference to specific embodiments, it will be apparent to one skilled in the art that various changes and modifications can be made without departing from the spirit and scope of the invention. Thus, it is intended that the invention covers the modifications and variations of this invention provided they come within the scope of the appended claims and their equivalents. It is expressly intended, for example, that all ranges broadly recited in this document include within their scope all narrower ranges which fall within the broader ranges. It is also intended that the components of the various devices disclosed above may be combined or modified in any suitable configuration.

What is claimed is:

1. An assembly for locking a fastener in a fixation plate, the fastener having a shaft with a plurality of threads, the assembly comprising:
   a locking element at least partially positioned in the fixation plate, the locking element having a base member and a head portion, the base member having an interlock portion configured to engage the threads of the fastener when in a locked position and configured to not engage the threads of the fastener when in an unlocked position, the interlock portion includes a plurality of elongated protrusions having a recess positioned between adjacent protrusions, a portion of an outer surface of each of the plurality of elongated protrusions contacts the shaft of the fastener when in the locked position, and the head portion extending from the base member, the head portion configured to be engaged by a driver to rotate the base member from the unlocked position to the locked position.

2. The assembly of claim 1, wherein each recess is configured to receive a portion of the plurality of threads of the fastener.

3. The assembly of claim 1, wherein the plurality of elongated protrusions includes three substantially parallel protrusions.

4. The assembly of claim 1, wherein the locking element includes a shaft between the base member and the head portion, the shaft having a smaller diameter than the head portion of the locking element.

5. The assembly of claim 1, wherein the base member is positioned inside the fixation plate.

6. The assembly of claim 1, wherein the fastener is a bone screw having a head and the shaft extending therefrom.

7. A system for preventing a fastener from backing out of a fixation plate, the system comprising:
   a fastener having a shaft with a plurality of threads;
   a locking element comprising:
      a base member having an interlock portion configured to engage the plurality of threads of the fastener when in a locked position and configured to not engage the threads of the fastener when in an unlocked position, the interlock portion includes a plurality of elongated protrusions having a recess positioned between adjacent protrusions, a portion of an outer surface of each of the plurality of elongated protrusions contacts the shaft of the fastener when in the locked position; and
      a head portion extending from the base member, the head portion configured to be engaged by a driver to rotate the base member from the unlocked position to the locked position; and
   a fixation plate having a bottom surface configured to engage a portion of a bone being fixated, an opposite top surface, an opening defined therethrough sized and configured to receive at least a portion of the fastener, and a blind opening for receiving the locking element positioned adjacent to the opening for receiving the fastener.

8. The system of claim 7, wherein the locking element includes a shaft between the base member and the head portion, the shaft having a smaller diameter than the head portion of the locking element.

9. The system of claim 7, wherein the blind opening includes a ridge configured to prevent the locking element from being removed axially.

10. The system of claim 9, wherein the ridge is configured to engage a bottom surface of the head portion.

11. The system of claim 7, wherein each recess is configured to receive a portion of the plurality of threads of the fastener.

12. The system of claim 7, wherein the plurality of elongated protrusions includes three substantially parallel protrusions.

13. The system of claim 7, wherein the locking element is positioned inside the fixation plate.

14. A method of locking a bone screw in a fixation plate, the method comprising:
   inserting a fastener through an opening in a fixation plate and into contact with bone, the fastener having a shaft with a plurality of threads configured to engage the bone;
   locking the fastener to the fixation plate by rotating a locking element in the fixation plate from an unlocked position where an interlock portion on the locking element does not engage at least a portion of the plurality of threads of the fastener to a locked position such that the interlock portion on the locking element engages at least a portion of the plurality of threads of the fastener, the interlock portion includes a plurality of elongated protrusions having a recess positioned between adjacent protrusions, a portion of an outer surface of each of the plurality of elongated protrusions contacts the shaft of the fastener when in the locked position.

15. The method of claim 14, further comprising, before the fastener is inserted in the fixation plate, placing the locking element through the opening in the fixation plate and seating the locking element in a blind opening in the fixation plate.

16. The method of claim 14, wherein a driver engages a recess in the locking element to rotate the locking element.

* * * * *